(12) United States Patent
Berg-Schultz

(10) Patent No.: US 7,611,696 B2
(45) Date of Patent: Nov. 3, 2009

(54) SUNSCREEN COMPOSITIONS AS WELL AS DIHYDROPYRIDINES AND DIHYDROPYRANES

(75) Inventor: Katja Berg-Schultz, Kaiseraugst (CH)

(73) Assignee: DSM IP Assets B.V., Te Heerlen (NL)

( * ) Notice: Subject to any disclaimer, the term of this patent is extended or adjusted under 35 U.S.C. 154(b) by 747 days.

(21) Appl. No.: 10/494,500

(22) PCT Filed: Feb. 4, 2003

(86) PCT No.: PCT/EP03/01049

§ 371 (c)(1),
(2), (4) Date: Sep. 17, 2004

(87) PCT Pub. No.: WO03/068183

PCT Pub. Date: Aug. 21, 2003

(65) Prior Publication Data

US 2005/0019278 A1    Jan. 27, 2005

(30) Foreign Application Priority Data

Feb. 12, 2002 (EP) .................. 02002093

(51) Int. Cl.
*A61Q 17/04* (2006.01)
*C07D 211/68* (2006.01)
*C07D 309/00* (2006.01)
*A61K 8/18* (2006.01)

(52) U.S. Cl. .............. 424/59; 546/193; 549/356; 549/381

(58) Field of Classification Search .......... 424/59; 546/193; 549/356, 381
See application file for complete search history.

(56) References Cited

U.S. PATENT DOCUMENTS 4,937,370 A * 6/1990 Sabatelli ............... 560/45
5,605,680 A   2/1997 Deflandre et al.

FOREIGN PATENT DOCUMENTS

EP    0 780 119 A1    6/1997

OTHER PUBLICATIONS

R. Wortmann, Highly Transparent and Birefringent Chromophores for Organic Photorefractive Materials, 1999, Chemical Physics, vol. 245, pp. 107-120.*
Klemm, L.H. et al.,"Chemistry of Thienopyridines. XLII. Three Novel Compounds Derived from Thienopyridine N-Oxides [1]," *J. Heterocyclic Chem.*, vol. 31(1), 261-3 (1994).
Klemm, L.H. et al, "Chemistry of Thienopyridines. XXXV. Synthesis, Tautomerism, and Reactions of Quinoline and Thienopyridine Systems Which Bear a 1-Carboethoxy-1-Cyanomethyl Substituent in the Pyridine Ring. Part 2 [1,2]," *J. Heterocyclic Chem.*, vol. 24(5), 1467-72 (1987).
Klemm, L.H. et al., "Chemistry of Thienopyridines. XXXII. Direct Introduction of C-Substituents gamma to the Heteronitrogen Atom in the Thieno[2,3-b]pyridine System," *J. Heterocyclic Chem.*, vol. 21(4), 1135-40 (1984).

* cited by examiner

*Primary Examiner*—Johann R Richter
*Assistant Examiner*—Andriae M Holt
(74) *Attorney, Agent, or Firm*—Bryan Cave LLP

(57) ABSTRACT

1,4-dihydropyridine and 1,4-dihydropyrane derivatives and novel cosmetic or dematological sunscreen compositions containing novel and/or known 1,4-dihydropyridine or 1,4-dihydropyrane derivatives which are useful for photoprotecting human skin and/or hair against UV radiation, in particular solar radiation, and the use of such 1,4-dihydropyridine and/or 1,4-dihydropyrane derivatives as UV-A screening agents, particularly in cosmetic and pharmaceutical compositions.

17 Claims, No Drawings

SUNSCREEN COMPOSITIONS AS WELL AS DIHYDROPYRIDINES AND DIHYDROPYRANES

This application is the National Stage of International Application No. PCT/EP03/01049, filed Feb. 4, 2003.

The present invention relates to novel 1,4-dihydropyridine and 1,4-dihydropyrane derivatives, to novel cosmetic or dermatological sunscreen compositions containing certain novel and/or known 1,4-dihydropyridine or 1,4-dihydropyrane derivatives which are useful for photoprotecting human skin and/or hair against UV radiation, in particular solar radiation, and to the use of such 1,4-dihydropyridine and/or 1,4-dihydropyrane derivatives as UV-A screening agents, particularly in cosmetic and pharmaceutical compositions.

More particularly, in one aspect the invention relates to novel cosmetic or dermatological sunscreen compositions comprising a 1,4-dihydropyridine derivative of the general formula I or a 1,4-dihydropyrane derivative of the general formula II

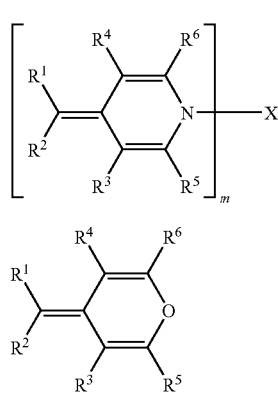

wherein m is 1 or 2;

$R^1$ and $R^2$ are identical or different electron-withdrawing groups, or one of $R^1$ and $R^2$ is hydrogen and the other of $R^1$ and $R^2$ is an electron-withdrawing group;

$R^3$, $R^4$, $R^5$, are $R^6$ are, independently, hydrogen, alkyl, cycloalkyl or aryl;

$R^3$ and $R^5$ and/or $R^4$, and $R^6$ taken together with the carbon atoms to which they are attached, may form a 5 or 6 membered ring which optionally is substituted with one to four alkyl, cycloalkyl or alkoxy groups;

X is a moiety $R^7$, when m is 1; and is alkylene or poly (oxyalkylene) when m is 2; and $R^7$ is hydrogen, alkyl, cycloalkyl, alkoxyalkyl or aryl.

As used herein the term "electron-withdrawing groups" refers to groups containing a multiple bond such as a nitrilo (—CN) group or a —$COOR^8$, —$COR^8$ or —$CONR(R^8)_2$ group, wherein $R^8$ is hydrogen, alkyl, cycloalkyl or aryl. Alkyl, alone and in combination with alkoxy refers to saturated straight or branched chain hydrocarbon groups containing 1 to 21, preferably 1 to 8 carbon atoms, such as methyl, ethyl, propyl, isopropyl, butyl, sec. butyl, isobutyl, pentyl, neopentyl, hexyl, 2-ethyl-hexyl, and octyl. Alkoxy, alone and in combination with alkyl refers to alkyl groups as defined above which are bound through an oxygen.

Aryl refers to aromatic, optionally substituted hydrocarbon groups such phenyl or phenyl groups substituted by one to three alkyl of 1 to 6 carbon atoms, by halogen, by hydroxy or by alkoxy of 1 to 6 carbon atoms or by a mixture thereof, or naphthyl residues.

Alkoxyalkyl refers to alkyl groups as defined earlier which are interrupted by an oxygen atom, such as methoxymethyl, methoxyethyl, ethoxyethyl, 3-(2-ethylhexyloxy)propyl etc.

Alkylene refers to alkyl groups as defined above which have an additional free valence bond, such as methylene, ethylene, 1,3-propylene, 1,2-propylene, 1,4-butylene, 1,5-pentylene, 1,6-hexylene, and 1,8-octylene.

The term poly(oxyalkylene) as used herein denotes a compound containing a polyether backbone. The polyether backbone can be based e.g. on propyleneoxide (PO), ethyleneoxide (EO) or mixed EO/PO. Examples of poly(oxyalkylene) are —$(R^9$—O—$R^{10})_x$—O—$(R^{11}$—O—$R^{12})_y$—, wherein $R^9$, $R^{10}$, $R^{11}$ and $R^{12}$ are, independently, methylene, ethylene, propylene or isopropylene, and x and y are, independently 1,2 or 3.

The compounds of the general formulas I and II above can be prepared according to procedures known in the art. Preferably, the compounds of the general formula I and II can be prepared by reacting a compound of the general formula III

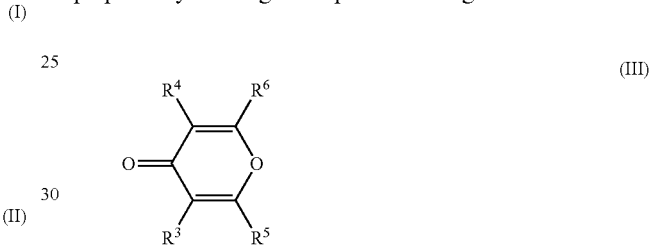

wherein $R^1$ through $R^6$ have the meanings given earlier, with a compound of the general formula IV

wherein $R^1$ and $R^2$ have the meanings given earlier, to yield a compound of the general formula II and, if required, reacting the compound of the formula II with a compound of the general formula V

wherein $R^7$ has the meanings given earlier, to yield a compound of the general formula I wherein m is 1 and X is $R^7$;

or with an α,ω-diamino-alkane, or with an α,ω-diamino-poly(oxyalkylene), e.g., a compound of the general formula VI

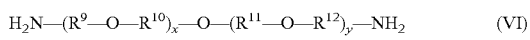

wherein $R^9$, $R^{10}$, $R^{11}$,$R^{12}$, x and y are as defined earlier, to yield a compound of the general formula I wherein m is 2 and X is alkylene or poly(oxyalkylene).

The condensation of a compound of formula III with a compound of formula IV can be accomplished by reacting the compounds in acetic anhydride at elevated temperature such as heating to reflux and work-up of the reaction mixture by removal of the acetic anhydride, extraction of the residue with ether and chromatography. The compound of formula II can be converted into a compound of the formula I by reaction with the appropriate amine V or VI at elevated temperature, e.g. at reflux temperature of the reaction mixture. The starting compounds of formula III, V and VI are known or belong to a class of known compounds and can be prepared by methods known per se and/or described hereinafter.

The above formulae I and II encompass novel compounds which, as such, are also an object of the present invention. The novel compounds include compounds of formulae I and II wherein $R^3$ and $R^4$ are alkyl, or wherein $R^3$ and $R^5$ and/or $R^4$, and $R^6$ taken together with the carbon atoms to which they are attached, form a 5 or 6 membered ring which optionally is substituted with one to four alkyl or alkoxy groups; and compounds of formula I, wherein m is 2.

In formula I the following significances are preferred independently, collectively or in any combination or sub-combination:
(a) $R^1$ and $R^2$ are, independently, a group —CN, COOR$^8$, COR$^8$ or CON(R$^8$)$_2$ wherein $R^8$ is hydrogen, alkyl, cycloalkyl or aryl; e.g. $R^1$ and $R^2$ are a group —CN or $R^1$ is a group —CN and $R^2$ is a group COOR$^8$.
(b) m is 1 or 2.
(c) $R^3$ and $R^4$ are hydrogen and $R^5$ and $R^6$ are alkyl or cycloalkyl.
(d) $R^7$ is alkyl, cycloalkyl or alkoxyalkyl.
(e) $R^2$ is a group COOR$^8$ and $R^8$ is alkyl.
(f) X is a group —(R$^9$—O—R$^{10}$)$_x$—O—(R$^{11}$—O—R$^{12}$)$_y$—, wherein $R^9$, $R^{10}$, $R^{11}$ and $R^{12}$ are, independently, methylene, ethylene or propylene, and x and y are, independently 1,2 or 3.

In formula II the following significances are preferred independently, collectively or in any combination or sub-combination:
(a) $R^1$ and $R^2$ are, independently, a group —CN, COOR$^8$, COR$^8$ or CON(R$^8$)$_2$, e.g. $R^1$ and $R^2$ are a group —CN or $R^1$ is a group —CN and $R^2$ is a group COOR$^8$.
(b) $R^3$ and $R^4$ are hydrogen and $R^5$ and $R^6$ are alkyl or cycloalkyl.
(c) $R^3$, $R^4$, $R^5$ and $R^6$ are alkyl or cycloalkyl.

Preferred compounds for use in the present invention are compounds of the formula I. From the compounds of the formula I, those wherein m is 1 and both $R^1$ and $R^2$ are a group —CN, or $R^1$ is a group —CN and $R^2$ is a group COOR$^8$, $R^3$ and $R^4$ are hydrogen, $R^5$ and $R^6$ are alkyl, and $R^7$ is alkyl or alkoxyalkyl are preferred. $R^8$ is preferably alkyl. From the compounds of the formula I, wherein m is 2 those, are preferred wherein $R^1$ and $R^2$ are a group —CN, and, further, X is —(R$^9$—O—R$^{10}$)$_x$—O—(R$^{11}$—O—R$^{12}$)$_y$—, wherein $R^9$, $R^{10}$, $R^{11}$ and $R^{12}$, x and y are as defined earlier.

Specifically, novel compounds included within the scope of the present invention are
2-{1-[3-(2-{2-[3-(4-dicyanomethylene-2,6-dimethyl-4H-pyridin-1-yl)-propoxy]-ethoxy}-ethoxy)-propyl]-2,6-dimethyl-1H-pyridin-4-ylidene}-malononitrile,
1-N-(2-ethylhexyl)-4-dicyanomethylene-2,6-dimethyl-1,4-dihydropyridine,
1-N-dodecyl-4-dicyanomethylene-2,6-dimethyl-1,4-dihydropyridine,
1-N-[3-(2-ethylhexyloxy)propyl]-4-dicyanomethylene-2,6-dimethyl-1,4-dihydropyridine,
1-N-[3,5,5-trimethylhexyl]-4-dicyanomethylene-2,6-dimethyl-1,4-dihydropyridine,
2-ethylhexyl (1-N-[3-(2-Ethylhexyloxy)propyl]-2,6-dimethyl-1H-pyridin-4-ylidene)cyanoacetate,
2-ethylhexyl (2,6-dimethylpyran-4-ylidene)cyanoacetate,
2-(2,6-diethyl-3,5-dimethylpyran-4-ylidene)malononitrile, and
2-(3,5-diethyl-2,6-dipropylpyran-4-ylidene)malononitrile.

The present invention also relates to compositions comprising a compound of formula I or II, formulated into a suitable support or substrate. Typically, the compositions of the invention are adopted for protecting a material that is sensitive to ultraviolet radiation, in particular solar radiation, and comprises an effective photoprotective amount of at least one of the compounds of formula I or II. In one preferred embodiment of the invention such compositions are suited for protecting the skin and/or hair against the deleterious effects of UV-radiation. In this case, the compositions according to the invention are cosmetic compositions which comprise a topically applicable, cosmetically-acceptable vehicle, diluent as carrier. According to another embodiment of the invention, the compounds of formula I or II can be incorporated into a plastic substrate. Compounds I and/or II may also be used to stabilize photosensitive ingredients in topical formulations particulary colorants, such as FD&C and D&C colorants, curcumin, riboflavin, lactoflavine, tartrazine, chinolinyellow, cochenille, azorubin, amaranth, ponceau 4R, erythrosin, indigotin, chlorophylle, chlorophyllin, caramel, Carbo medicinalis, carotinoids, bixin, norbixin, annato, orlean, capsanthin, capsorubin, lycopin, xanthophylle, flavoxanthin, lutein, kryptoaxanthin, rubixanthin, violaxanthin, rhodoxanthin, canthaxanthin, betanin, anthocyans, vitamins such as vitamin A, vitamin K1, vitamin C or other active ingredients.

The compounds of formula I and II have adsorption maxima in the UV-A region. For the preparation of light screening agents, especially of preparations for dermatological and/or cosmetic use, such as skin protection and sunscreen formulations for everyday cosmetics a compound of formula I or II may be incorporated in auxiliary agents, e.g. a cosmetic base, which are conventionally used for such formulations. Where convenient, other conventional UV-A and/or UV-B screening agents, preferably a pigment, may also be added. The combination of UV filters may show a synergistic effect. The preparation of said light screening agents is well known to the skilled artisan in this field. The concentration of UV filters is varied in a wide range. For example, the amount of compounds of formula I or II and optionally an additional hydrophilic and/or lipophilic UV-A or UV-B screening agent other than the compounds of formula I or II may be in the range of from 0.5 to 12% by weight of the total composition. These additional screening agents are advantageously selected from the compounds listed below without being limited thereto:

Examples of UV B screening agents, i.e. substances having absorption maxima between about 290 and 320 nm, which come into consideration for combination with the compounds of the present invention are, e.g., the following organic and inorganic compounds:

acrylates such as 2-ethylhexyl 2-cyano-3,3-diphenylacrylate (octocrylene, PARSOL® 340), ethyl 2-cyano-3,3-diphenylacrylate and the like;

camphor derivatives such as 4-methyl benzylidene camphor (PARSOL® 5000), 3-benzyl-idene camphor, camphor benzalkonium methosulfate, polyacrylamidomethyl benzyl-idene camphor, sulfobenzylidene camphor, sulfomethyl benzylidene camphor, therephthalidene dicamphor sulfonic acid and the like;

cinnamate derivatives such as octyl methoxycinnamate (PARSOL® MCX), ethoxyethyl methoxycinnamate, diethanolamine methoxycinnamate (PARSOL® Hydro), isoamyl methoxycinnamate and the like as well as cinnamic acid derivatives bond to siloxanes;

p-aminobenzoic acid derivatives, such as p-aminobenzoic acid, 2-ethylhexyl p-dimethyl-aminobenzoate, N-oxypropylenated ethyl p-aminobenzoate, glyceryl p-amino-benzoate, benzophenones such as benzophenone-3, benzophenone-4,2, 2',4,4'-tetrahydroxy-benzophenone, 2,2'-dihydroxy-4,4'-dimethoxybenzophenone and the like;

esters of benzalmalonic acid such as di(2-ethylhexyl) 4-methoxybenzalmalonate;

esters of 2-(4-ethoxy anilinomethylene)propanedioic acid such as 2-(4-ethoxy anilinomethylene)propanedioic acid diethyl ester as described in EP 895,776;

organosiloxane compounds containing benzmalonate groups as described in EP 358,584, EP 538,431 and EP 709,080;

drometrizole trisiloxane (MEXORYL XL);

pigments such as microparticulated $TiO_2$, and the like, wherein the term "microparticulated" refers to a particle size from about 5 nm to about 200 nm, particularly from about 15 nm to about 100 nm, and which $TiO_2$ particles may be coated by metal oxides such as e.g. aluminum or zirconium oxides or by organic coatings such as e.g. polyols, methicones, aluminum stearate, alkyl silane;

imidazole derivatives such as e.g. 2-phenyl benzimidazole sulfonic acid and its salts (PARSOL® HS). Salts of 2-phenyl benzimidazole sulfonic acid are e.g. alkali salts such as sodium- or potassium salts, ammonium salts, morpholine salts, salts of primary, sec. and tert. amines like monoethanolamine salts, diethanolamine salts and the like;

salicylate derivatives such as isopropylbenzyl salicylate, benzyl salicylate, butyl salicylate, octyl salicylate (NEO HELIOPAN OS), isooctyl salicylate or homomethyl salicylate (homosalate, HELIOPAN) and the like;

triazine derivatives such as octyl triazone (UVINUL T-150), dioctyl butamido triazone (UVASORB HEB), bis ethoxyphenol methoxyphenyl triazine (TINOSORB S) and the like;

encapsulated 2-ethylhexyl-4-methoxy cinnamate such as Eusolex® UV-pearls™ OMC and the like.

Examples of UVA screening agents i.e. substances having absorption maxima between about 320 and 400 nm, which come into consideration for combination with the compounds of the present invention are, e.g., the following organic and inorganic compounds:

dibenzoylmethane derivatives such as 4-tert. butyl-4'-methoxydibenzoyl-methane (PARSOL® 1789), dimethoxydibenzoylmethane, isopropyldibenzoylmethane and the like;

benzotriazole derivatives such as 2,2'-methylene-bis-(6-(2H-benzotriazole-2-yl)-4-(1,1,3,3,-tetramethylbutyl)-phenol (TINOSORB M) and the like;

phenylene-1,4-bis-benzimidazolsulfonic acids or salts such as 2,2-(1,4-phenylene)bis-(1H-benzimidazol-4,6-disulfonic acid) (NEOHELIOPAN AP);

amino substituted hydroxybenzophenones such as 2-(4-diethylamino-2-hydroxy-benzoyl)-benzoic acid hexylester as described in EP 1,046,391;

pigments such as microparticulated ZnO and the like, wherein the term "microparticulated" refers to a particle size from about 5 nm to about 200 nm, particularly from about 15 nm to about 100 nm, and which ZnO particles may be coated by metal oxides such as e.g. aluminum or zirconium oxides or by organic coatings such as e.g. polyols, methicones, aluminum stearate, alkyl silane.

As dibenzoylmethane derivatives have limited photostability it may be desirable to photostabilize these UV-A screening agents. Thus, the term "conventional UV-A screening agent" also refers to dibenzoylmethane derivatives such as e.g. PARSOL® 1789 stabilized by, e.g., 3,3-diphenylacrylate derivatives as described in EP 514,491 and EP 780,119;

benzylidene camphor derivatives as described in U.S. Pat. No. 5,605,680;

organosiloxanes containing benzmalonate groups as described in EP 358,584, EP 538,431 and EP 709,080.

The compositions of the invention may also contain usual cosmetic adjuvants and additives, such as preservatives/antioxidants, fatty substances/oils, water, organic solvents, silicones, thickeners, softeners, emulsifiers, additional sunscreens, antifoaming agents, moisturizers, fragrances, surfactants, fillers, sequestering agents, anionic, cationic, nonionic or amphoteric polymers or mixtures thereof, propellants, acidifying or basifyng agents, dyes, colorants, pigments or nanopigments, in particular those suited for providing an additional photoprotective effect by physically blocking out ultraviolet radiation, or any other ingredients usually formulated into cosmetics, in particular for the production of sunscreen/antisun compositions. The necessary amounts of the cosmetic and dermatological adjuvants and additives may, based on the desired product, easily be chosen by a skilled artisan in this field and will be illustrated in the examples, without being limited hereto.

An additional amount of antioxidants/preservatives is generally preferred. All known antioxidants usually formulated into cosmetics may be used. Especially preferred are antioxidants chosen from the group consisting of amino acids (e.g. glycine, histidine, tyrosine, tryptophane) and their derivatives, imidazole (e.g urocanic acid) and derivatives, peptides such as D,L-carnosine, D-carnosine, L-carnosine and derivatives (e.g. anserine), carotinoids, carotenes (e.g. α-carotene, β-carotene, lycopene) and derivatives, chlorogenic acid and derivatives, liponic acid and derivatives (e.g. dihydroliponic acid), aurothioglucose, propylthiouracil and other thiols (e.g. thioredoxine, glutathione, cysteine, cystine, cystamine and its glycosyl-, N-acetyl-, methyl-, ethyl-, propyl-, amyl-, butyl- and lauryl-, palmitoyl-; oleyl-, y-linoleyl-, cholesteryl- and glycerylester) and the salts thereof, dilaurylthiodipropionate, distearylthiodipropionate, thiodipropionic acid and its derivatives (ester, ether, peptides, lipids, nucleotides, nucleosides and salts) as well as sulfoximine compounds (such as buthionine sulfoximine, homocysteine sulfoximine, buthionine sulfone, penta-, hexa-, heptathionine sulfoximine) in very low compatible doses (e.g. pmol/kg to µmol/kg), additionally (metal)-chelators (such as α-hydroxyfatty acids, palmic-, phytinic acid, lactoferrin), α-hydroxyacids (such as citric acid, lactic acid, malic acid), huminic acid, gallic acid, gallic extracts, bilirubin, biliverdin, EDTA, EGTA and its derivatives, unsaturated fatty acids and their derivatives (such as γ-linoleic acid, linolic acid, oleic acid), folic acid and its derivatives, ubiquinone and ubiquinol and their derivatives, vitamine C and derivatives (such as ascorbyl palmitate and ascorbyl tetraisopalmitate, Mg-ascorbyl phosphate, Na-ascorbyl phosphate, ascorbyl acetate), tocopherol and derivates (such as vitamin-E-acetate, nat. vitamin E and mixtures thereof), vitamin A and derivatives (vitamin A palmitate and acetate) as well as coniferylbenzoat, rutinic acid and derivatives, α-glycosylrutin, ferulic acid, furfurylidene glucitol, butyl hydroxytoluene, butyl hydroxyanisole, trihydroxybutyrophenone, urea and its derivatives, mannose and derivatives, zinc and derivatives (e.g. ZnO, $ZnSO_4$), selenium and derivatives, (e.g. selenomethionine) stilbenes and derivatives (such as stilbenoxide, transstilbenoxide) and suitable derivatives (salts, esters, ethers, sugars, nucleotides, nucleosides, peptides and lipids) of the named active ingredients. One or more preservatives/antioxidants maybe present in an amount of about 0.01 wt. % to about 10 wt. % of the total weight of the composition of the present invention. Preferably, one or more preservatives/antioxidants are present in an amount of about 0.1 wt. % to about 1 wt. %.

Examples of emulsifiers that maybe used in the present invention in order to form O/W, W/O, O/W/O or W/O/W emulsions/microemulsions include sorbitan oleate, sorbitan sesquioleate, sorbitan isostearate, sorbitan trioleate, polyglyceryl-3-diisostearate, polyglycerol esters of oleic/isostearic acid, polyglyceryl-6 hexaricinolate, polyglyceryl-4-oleate, polygylceryl-4 oleate/PEG-8 propylene glycol cocoate, oleamide DEA, TEA myristate, TEA stearate, magnesium stearate, sodium stearate, potassium laurate, potassium ricinoleate, sodium cocoate, sodium tallowate, potassium castorate, sodium oleate, and mixtures thereof. Further suitable emulsifiers are phosphate esters and the salts thereof such as cetyl phosphate (Amphisol® A), diethanolamine cetyl phosphate (Amphisol®), potassium cetyl phosphate (Amphisol® K), sodium glyceryl oleate phosphate, hydrogenated vegetable glycerides phosphate and mixtures thereof. Furthermore, one or more synthetic polymers may be used as an emulsifier. For example, PVP eicosene copolymer, acrylates/$C_{10-30}$alkyl acrylate crosspolymer, acrylates/steareth-20 methacrylate copolymer, PEG-22/dodecyl glycol copolymer, PEG-45/dodecyl glycol copolymer, and mixtures thereof. The preferred emulsifiers are cetyl phosphate (Amphisol® A), diethanolamine cetyl phosphate (Amphisol®), potassium cetyl phosphate (Amphisol® K), PVP eicosene copolymer, acrylates/-$C_{10-30}$alkyl acrylate crosspolymer, PEG-20 sorbitan isostearate, sorbitan isostearate, and mixtures thereof. Emulsifiers are present in a total amount of about 0.01 wt. % to about 20 wt. % of the total weight of the composition of the present invention. Preferably, about 0.1 wt. % to about 10 wt. % of emulsifier are used.

The lipid phase may advantageously be chosen from mineral oils and mineral waxes; oils such as triglycerides of caprinic acid or caprylic acid, preferably castor oil; oils or waxes and other natural or synthetic oils, in a preferred embodiment esters of fatty acids with alcohols e.g. isopropanol, propyleneglycol, glycerin or esters of fatty alcohols with lower carboxylic acids or fatty acids; alkylbenzoates; silicone oils such as dimethylpolysiloxane, diethylpolysiloxane, diphenylpolysiloxane, cyclomethicone and mixtures thereof.

Exemplary fatty substances which may be incorporated into the oil phase of the emulsion, microemulsion, oleo gel, hydrodispersion or lipodispersion of the present invention are advantageously chosen from esters of saturated and/or unsaturated, linear or branched alkyl carboxylic acids with 3 to 30 carbon atoms, and saturated and/or unsaturated, linear and/or branched alcohols with 3 to 30 carbon atoms as well as esters of aromatic carboxylic acids and of saturated and/or unsaturated, linear or branched alcohols of 3-30 carbon atoms. Such esters may advantageously be selected from octylpalmitate, octylcocoate, octylisostearate, octyldodeceylmyristate, cetearylisononanoate, isopropylmyristate, isopropylpalmitate, isopropylstearate, isopropyloleate, n-butylstearate, n-hexyllaureate, n-decyloleat, isooctylstearate, isononylstearate, isononylisononanoate, 2-ethyl hexylpalmitate, 2-ethylhexyllaurate, 2-hexyldecylstearate, 2-octyldodecylpalmitate, stearylheptanoate, oleyloleate, oleylerucate, erucyloleate, erucylerucate, tridecylstearate, tridecyltrimellitate, and synthetic, half-synthetic or natural mixtures of such esters e.g. jojoba oil.

Other fatty components suitable for use in the formulation of the present invention include polar oils such as lecithines and fatty acid triglycerides, namely triglycerinic esters of saturated and/or unsaturated, straight or branched carbonic acid with 8 to 24 carbon atoms, preferably of 12 to 18 carbonatoms whereas the fatty acid triglycerides are preferably chosen from synthetic, half synthetic or natural oils (e.g. cocoglyceride, olive oil, sun flower oil, soybean oil, peanut oil, rape seed oil, sweet almond oil, palm oil, coconut oil, castor oil, hydrogenated castor oil, wheat oil, grape seed oil, macadamia nut oil and others); apolar oils such as linear and/or branched hydrocarbons and waxes e.g. mineral oils, vaseline (petrolatum); paraffins, squalan and squalen, polyolefines, hydrogenated polyisobutenes and isohexadecanes, favored polyolefines are polydecenes; dialkyl ethers such as dicaprylylether; linear or cyclic silicone oils such as preferably cyclomethicone (octamethylcyclotetrasiloxane), cetyldimethicone, hexamethylcyclotrisiloxane, polydimethylsiloxane, poly(methylphenylsiloxane) and mixtures thereof.

Still other fatty components which may advantageously be incorporated into formulations of the present invention include isoeikosane; neopentylglycol diheptanoate; propyleneglycol dicaprylate/dicaprate; caprylic/capric/diglycerylsuccinate; butyleneglycol caprylate/caprate; $C_{12-15}$alkyllactates; di-$C_{12-15}$alkyltartrates; triisostearin; dipentaerythrityl hexacaprylate/hexacaprate; propyleneglycol monoisostearate; tricaprylin; dimethylisosorbid. Especially beneficial is the use of mixtures of $C_{12-15}$alkylbenzoates and 2-ethylhexylisostearate, mixtures of $C_{12-15}$alkylbenzoates and isotridecylisononanoate as well as mixtures of $C_{12-15}$alkylbenzoates, 2-ethylhexylisostearate and isotridecylisononanoate.

The oily phase of the formulation of the present invention may also contain natural vegetable or animal waxes such as bee wax, china wax, bumblebee wax and other waxes of insects as well as shea butter and cocoa butter.

A moisturizing agent may be incorporated into a composition of the present invention to maintain hydration or rehydrate the skin. Moisturizers that prevent water from evaporating from the skin by providing a protective coating are called emollients. Additionally an emollient provides a softening or soothing effect on the skin surface and is generally considered safe for topical use. Preferred emollients include mineral oils, lanolin, petrolatum, capric, caprylic triglyceraldehydes, cholesterol, silicones such as dimethicone, cyclomethicone, almond oil, jojoba oil, avocado oil, castor oil, sesame oil, sunflower oil, coconut oil and grape seed oil, cocoa butter, olive oil aloe extracts, fatty acids such as oleic and stearic, fatty alcohols such as cetyl and hexadecylalcohol, diisopropyl adipate, hydroxybenzoate esters, benzoic acid esters of $C_{9-15}$-alcohols, isononyl iso-nonanoate, ethers such as polyoxypropylene butyl ethers and polyoxypropylene cetyl ethers, and $C_{12-15}$alkyl benzoates, and mixtures thereof. The most preferred emollients are hydroxybenzoate esters, aloe vera, $C_{12-15}$alkyl benzoates, and mixtures thereof. An emollient may be present in an amount of about 1 wt. % to about 20 wt. % of the total weight of the composition. The preferred amount of emollient may be about 2 wt. % to about 15 wt. %, and most preferably about 4 wt. % to about 10 wt. %.

Moisturizers that bind water, thereby retaining it on the skin surface are called humectants. Suitable humectants may be incorporated into a composition of the present invention such as glycerin, polypropylene glycol, polyethylene glycol, lactic acid, pyrrolidon carboxylic acid, urea, phopholipids, collagen, elastin, ceramides, lecithin sorbitol, PEG-4, and mixtures thereof. Additional suitable moisturizers are polymeric moisturizers of the family of water soluble and/or swellable/ and/or with water gelating polysaccharides such as hyaluronic acid, chitosan and/or a fucose rich polysaccharide which is e.g. available as Fucogel® 1000 (CAS-Nr. 178463-23-5) by SOLABIA S. One or more humectants are optionally present at about 0.5 wt. % to about 8 wt. % in a composition of the present invention, preferably about 1 wt. % to about 5 wt. %.

The aqueous phase of the compositions of the present invention may contain usual cosmetic additives such as alcohols, especially lower alcohols, preferably ethanol and/or isopropanol, low diols oder polyols and their ethers, preferably propylenglycols, glycerin, ethyleneglycol, ethyleneglycol monoethyl- or monobutyl-ether, propylene glycol-monomethyl-, monoethyl- or monobutyl ether, diethylene glycolmonomethyl- or monoethylether and analogue products, polymers, foam stabilisators; electrolytes and especially one or more thickeners. Thickeners that may be used in formulations of the present invention to assist in making the consistency of a product suitable include carbomer, siliciumdioxide, magnesium and/or aluminum silicates, beewax, stearic acid, stearyl alcohol polysaccharides and their derivatives such as xanthan gum, hydroxypropyl cellulose, polyacrylamides, acrylate crosspolymers preferably a carbopole, such as carbopole of type 980, 981, 1382, 2984, 5984 alone or mixtures thereof. Suitable neutralizing agents which may be included in the composition of the present invention to neutralize components such as e.g. an emulsifier or a foam builder/stabilizer include but are not limited to alkali hydroxides such as a sodium and potassium hydroxide; organic bases such as diethanolamine (DEA), triethanolamine (TEA), aminomethyl propanol, and mixtures thereof; amino acids such as arginine and lysine and any combination of any foregoing. The neutralizing agent may be present in an amount of about 0.01 wt. % to about 8 wt. % in the composition of the present invention, preferably, 1 wt. % to about 5 wt. %.

The addition of electrolytes into the composition of the present invention may be necessary to change the behavior of a hydrophobic emulsifier. Thus the emulsions/microemulsions of this invention may preferably contain electrolytes of one or several salts including anions such as a chloride, a sulfate, a carbonate, a borate or an aluminate, without being limited thereto. Other suitable electrolytes may be on the bases of organic anions such as, but not limited to, lactate, acetate, benzoate, propionate, tartrate and citrate. As cations preferably ammonia, alkylammonia, alkali or alkaline earth metals, magnesium, iron or zinc ions are selected. Especially preferred salts are potassium and sodium chloride, magnesium sulfate, zinc sulfate and mixtures thereof. Electrolytes are present in an amount of about 0.01 wt. % to about 8 wt. % in the composition of the present invention.

The cosmetic compositions of the invention are useful as compositions for photoprotecting the human epidermis or hair against the damaging effect of ultraviolet irradiation, as antisun/sunscreen composition or as makeup product. Such compositions can, in particular, be provided in the form of a lotion, a thickened lotion, a gel, a cream, a milk, an ointment, a powder or a solid tube stick and may optionally be packaged as an aerosol and may be provided in the form of a mousse, foam or a spray. When the cosmetic composition according to the invention is provided for protecting the human epidermis against UV radiation or as antisun/sunscreen composition, it may be in the form of a suspension or dispersion in solvents or fatty substances, or alternatively in the form of an emulsion or microemulsion (in particular of O/W or W/O type, O/W/O or W/O/W-type), such as a cream or a milk, a vesicular dispersion, in the form of an ointment, a gel, a solid tube stick or an aerosol mousse. The emulsions can also contain anionic, nonionic, cationic or amphoteric surfactants.

When the cosmetic composition according to the invention is used for protecting the hair, it may be in the form of a shampoo, a lotion, a gel or a rinse out composition, to be applied before or after shampooing, before or after dyeing or bleaching, before, during or after permanent-waving or hair straightening operation, a styling or treatment lotion or a gel, a blow-drying or hairsetting lotion or gel, a hair lacquer, or a composition for permanent-waving, straightening, dyeing or bleaching the hair.

When the cosmetic composition according to the invention is used as makeup product for eyelashes, the eyebrows, the skin or the hair, such as an epidermal treatment cream, a foundation, a tube of lipstick, an eyeshadow, a face powder, an eyeliner, a mascara or a coloring gel, it may be solid or pasty, anhydrous or in aqueous form, such as O/W or W/O emulsion, suspension or gel.

The present invention also features formulating the compounds of formula I and II as an agent for screening out UV radiation, in particular for controlling the color of human skin.

This invention also features non-therapeutic regime/regimen for protecting the skin and/or hair against ultraviolet radiation, in particular solar radiation, comprising topically applying an effective amount of a cosmetic composition as described above, or of a compound of formula I or II.

Finally, this invention also features non-therapeutic regime/regimen for controlling the variation of the color of the skin caused by ultraviolet radiation, comprising topically applying onto the skin an effective amount of a cosmetic composition as described above, or of a compound of formula I or II.

The following examples are provided to further illustrate the processes and compositions of the present invention. These examples are illustrative only and are not intended to limit the scope of the invention in any way. In the Examples, FC. means Flash chromatography; HV means high vacuum (0.1 Pa or below).

EXAMPLE 1

Preparation of ethyl (2,6-dimethyl-pyran-4-ylidene) cyanoacetate

To a mixture of 9.45 ml (100 mmol) acetic anhydride and 1.06 ml (10 mmol) ethylcyano acetate 1.24 g (10 mmol) of 1,4-dimethyl-γ-pyrones was added. The reaction mixture was refluxed for 20 h at 155° C. After evaporation of the acetic anhydride the residue was extracted with ether (2×50 ml). The combined organic phases were subsequently washed with water (3×30 ml) and saturated NaCl-solution (1×30 ml). After drying ($Na_2SO_4$), the solvent was evaporated (HV) and the crude product purified via FC (n-hexane/EtOAC 7:3) yielding 0.15 g (7%) of ethyl (2,6-dimethyl-pyran-4-ylidene) cyanoacetate as a solid.

$^1$H-NMR (300 MHZ, $CDCl_3$): 7.90 (s, 1H), 6.60 (s, 1H), 4.2 (q, 2H, —$OCH_2$), 2.29 (s, 6H, $CH_3$), 1.32 (t, 3H, $CH_3$). MS (EI): 219 (100, M$^+$), 191 (13), 174 (83), 147 (64), 122 (9), 91 (4), 43 (11), 29 (3). IR (neat): 2987w, 2193s, 1697s, 1649vs, 1582s, 1513s, 1459m, 1407m, 1390w, 1362m, 1338s, 1251vs (br.), 1212s, 1173s, 1135s, 1059m, 1025m cm$^{-1}$. M.p.: 163-164° C., UV: $\lambda_{max}$=348 nm ($\epsilon$=24'982).

EXAMPLE 2

Preparation of 2-ethylhexyl (2,6-dimethyl-pyran-4-ylidene) cyanoacetate

To a suspension of 1.72 g (10 mmol) of (2,6-dimethyl-4H-pyran-4-ylidene)malononitril in 33 ml of 2-ethyl-1-hexanol, 3.3 ml of water and 3.3 ml of concentrated $H_2SO_4$ were added. The reaction mixture was refluxed at 100° C. for 48 h. After addition of 50 ml of water the resulting solution was extracted with ether (2×100 ml). The organic phase was washed with water (2×50 ml) and with saturated NaCl-solution (1×50 ml). After drying (Na$_2$SO$_4$), the solvent was evaporated (HV) and the crude product was purified via FC (n-hexane/EtOAC 85:15) yielding 1.71 g (56%) of 2-ethylhexyl (2,6-dimethyl-pyran-4-ylidene) cyanoacetate as a slightly yellow solid.

$^1$H-NMR (300 MHZ, CDCl$_3$): 7.90 (s, 1H), 6.60 (s, 1H), 4.08 (m, 2H, —OCH$_2$), 2.29 (s, 6H, CH$_3$), 1.65 (m, 1H), 1.50-1.20 (m, 8H), 0.90 (m, 6H, 2CH$_3$). MS (EI): 303 (28, M$^+$), 191 (100), 174 (41), 147 (27). IR (neat): 2958m, 2931m, 2873w, 2198m, 1696s, 1656vs, 1585m, 1523s, 1459m, 1410m, 1379w, 1341s, 1274m, 1252s (br.), 1213m, 1176m, 1131m, 1062m, 1038w cm$^{-1}$. M.p.: 64-65° C., UV: $\lambda_{max}$=352 nm ($\epsilon$=25'548).

EXAMPLE 3

Preparation of 2-(2,6-diethyl-3,5-dimethylpyran-4-ylidene)malononitrile

To a solution of 0.33 g (5 mmol) of malonodinitrile in 2.4 ml (25 mmol) acetic anhydride 1.20 g (5 mmol) of 2,6-diethyl-3,5-dipropyl-pyran-4-one (prepared according to J. Chem. Soc (C), 1967, 828-830) was added. After addition of 150 ml of water the resulting solution was extracted twice with ether (50 ml). The combined organic phases were washed with water (2×50 ml) and with saturated NaCl-solution (1×30 ml). After drying (Na$_2$SO$_4$), the solvent was evaporated (HV) and the crude product was purified via FC (n-hexane/EtOAC 7:3) yielding 0.54 g (47%) of 2-(2,6-diethyl-3,5-dimethylpyran-4-ylidene)malononitrile as a brown solid.

$^1$H-NMR (300 MHZ, CDCl$_3$): 2.64 (q, 4H, 2CH$_2$), 2.35 (s, 6H, 2CH$_3$) 1.21 (s, 6H, 2CH$_3$). MS (EI): 228 (100, M$^+$), 213 (3), 201 (5), 200 (5), 188 (48), 163 (9), 57 (8), 43 (3), 29 (4). IR (neat): 2986m, 2942m, 2343w (br.), 2193s, 1622vs, 1551s, 1428s (br.), 1387s, 1203m, 1189s, 1169s, 1082m, 1033s cm$^{-1}$. M.p.: 64-65° C., UV: $\lambda_{max}$=366 nm ($\epsilon$=22'808).

EXAMPLE 4

Preparation of 2-(3,5-diethyl-2,6-dipropylpyran-4-ylidene)malononitrile 2-(3,5-Diethyl-2,6-dipropylpyran-4-ylidene)malononitrile was prepared in analogy to the procedure of example 3.

$^1$H-NMR (300 MHZ, CDCl$_3$): 2.90 (q, 4H, 2CH$_2$) 2.60 (t, 4H, 2CH$_2$), 1.70 (m, 2H, 2CH$_2$), 1.22 (t, 6H, 2CH$_3$) 1.00 (t, 6H, 2CH$_3$). MS (EI): 284 (54, M$^+$), 269 (100), 256 (10), 244 (18), 230 (9), 216 (9), 203 (7), 71 (3), 43 (10). IR (neat): 2965m, 2934w, 2875w, 2198s, 1615vs, 1550w, 1443s (br.), 1379m, 1325w, 1255w, 1178m, 1155m, 1055m, 956m cm$^{-1}$, UV: $\lambda_{max}$=364 nm ($\epsilon$=21'729).

EXAMPLE 5

Preparation of 1-N-(2-ethylhexyl)-4-dicyanomethylene-2,6-dimethyl-1,4-dihydropyridine A solution of 0.5 g (2.9 mmol) of (2,6-dimethyl-4H-pyran-4-ylidene)malononitril in 7.6 ml (6 g, 46.4 mmol) 2-ethyl-1-hexylamine was refluxed for 1 h under nitrogen. Removal of the excess of ethyl-1-hexylamine at reduced pressure left a solid which was recrystallized from 15 ml EtOAc/MeOH 2/1 yielding 0.45 g (55%) of 1-N-(2-ethylhexyl)-4-dicyanomethylene-2,6-dimethyl-1,4-dihydropyridine.

$^1$H-NMR (300 MHZ, CDCl$_3$): 6.7 (s, 2H, H—C(3), H—C(5)), 3.85 (d, 2H, H—C(1')), 2.42 (s, 6H, —CH$_3$), 1.7 (m, 1H, H—C(2')), 1.41-1.12 (m, 8H, CH$_2$), 0.9 (2t, 6H, 2CH$_3$). MS (CI): 284.3 (M+H$^+$). IR (neat): 2966m, 2932m, 2860w, 2187s, 2164vs, 1638vs, 1552s, 1499s, 1469m, 1372s, 1347s, 1221m, 1185s, 1067m, 1036w cm$^{-1}$. M.p.: 187° C., UV: $\lambda_{max}$=372 nm ($\epsilon$=39'687).

EXAMPLE 6

Preparation of Compounds in Analogy to Example 1

In analogy to the procedure of Example 1, the following compounds were obtained:

1-N-dodecyl-4-dicyanomethylene-2,6-dimethyl-1,4-dihydropyridine.

$^1$H-NMR (300 MHZ, CDCl$_3$): 6.69 (s, 2H, H—C(3), H—C(5)), 3.88 (m, 2H, H—C(1')), 2.45 (s, 6H, —CH$_3$), 1.68 (m, 2H, H—C(2')), 1.45-1.20 (m, 19H, CH$_2$), 0.88 (t, 3H, —CH$_3$). MS (EI): 339 (M$^+$,100), 324 (73), 310 (13), 296(10), 282(12), 268 (10), 254 (13), 240 (8), 226 (6), 212 (7), 198 (8), 185 (14), 171 (27), 57 (10), 43 (15). IR (neat): 2914vs, 2815vs, 2189vs, 2163vs, 1644vs, 1554s, 1504m, 1472s, 1359s, 1314m, 1223m, 1188s, 1127w, 1069m, 1037w cm$^{-1}$. M.p.: 161-162° C. UV: $\lambda_{max}$=370 nm ($\epsilon$=42'538).

1-N-[3-(2-ethylhexyloxy)propyl]-4-dicyanomethylene-2,6-dimethyl-1,4-dihydropyridine.

$^1$H-NMR (300 MHZ, CDCl$_3$): 6.69 (s, 2H, H—C(3), H—C(5)), 4.05 (m, 2H, H—C(1')), 3.46 (t, 2H, H—C(3'), 3.31 (d, 2H, H—C(1")), 2.48 (s, 6H, —CH$_3$), 1.93 (m, 2H, H—C(2')), 1.50 (m, 2H, H—C(2")), 1.40-1.20 (m, 8H, CH$_2$), 0.90 (2t, 6H, 2CH$_3$). MS (CI): 342 (M+H$^+$). IR (neat): 2957m, 2928m, 2858m, 2189vs, 2163vs, 1644vs, 1553m, 1503m, 1482m, 1461m, 1379m, 1356vs, 1312w, 1223w, 1191s, 1107s (br.), 1068m, 1037m cm$^{-1}$. M.p.: 116-117° C. UV: $\lambda_{max}$=370 nm ($\epsilon$=37'846).

1-N-[3,5,5-trimethylhexyl]-4-dicyanomethylene-2,6-dimethyl-1,4-dihydropyridine.

$^1$H-NMR (300 MHZ, CDCl$_3$): 6.62 (s, 2H, H—C(3), H—C(5)), 3.9 (m, 2H, H—C(1')), 2.49 (s, 6H, —CH$_3$), 1.70 (m, 2H, H—C(2')), 1.55 (m, 2H, H—C(3')), 1.20 (m, 2H, H—C(4')), 1.05 (d, 2H, CH$_3$), 0.92 (s, 9H, 3CH$_3$). MS (CI): 298 (M+H$^+$). IR (neat): 2954m, 2192vs, 2171vs, 1626vs, 1554m, 1503m, 1481m, 1422w, 1388m, 1344vs, ,1224w, 1189s, 1107s, 1069m, 1036m cm$^{-1}$. M.p.: 236-237-117° C. UV: $\lambda_{max}$=372 nm ($\epsilon$=39'569).

1-N-methyl-4-dicyanomethylene-2,6-dimethyl-1,4-dihydropyridine.

$^1$H-NMR (300 MHZ, CDCl$_3$): 6.65 (s, 2H, H—C(3), H—C(5)), 3.61 (s, 3H, —NCH$_3$), 2.49 (s, 6H, —CH$_3$). MS (EI): 185 (M$^+$). IR (neat): 2962w, 2185vs, 2161vs, 1635vs, 1555s, 1495s, 1422m, 1383m, 1354vs, 1223w, 1195s, 1067s, 1038m cm$^{-1}$. M.p.: >250° C. UV:$\lambda_{max}$=368 nm ($\epsilon$=36'280).

1-N-butyl-4-dicyanomethylene-2,6-dimethyl-1,4-dihydropyridine.

$^1$H-NMR (300 MHZ, CDCl$_3$): 6.65 (s, 2H, H—C(3), H—C(5)), 3.90 (m, 2H, H—C(1')), 2.49 (s, 6H, —CH$_3$), 1.69 (m, 2H, H—C(2')), 1.45 (m, 2H, H—C(3')), 1.005 (s, 3H, —CH$_3$). MS (CI): 228 (M+H$^+$). IR (neat): 2956w, 2869w, 2191vs, 2167vs, 1633vs, 1553s, 1499s, 1479m, 1383m, 1361vs, 1338s, 1223m, 1185s, 1112m, 1067s cm$^{-1}$. M.p.: 198° C. UV: $\lambda_{max}$=370 nm ($\epsilon$=37'300).

EXAMPLE 7

Preparation of 2-ethylhexyl (1-N-butyl-2,6-dimethyl-1H-pyridin-4-ylidene)cyanoacetate A solution of 0.30 g (1 mmol) of 2-ethylhexyl (2,6-dimethyl-pyran-4-ylidene)cyanoacetate (prepared as described in example 1) in 4 ml butylamine was refluxed at 80° C. for 1 h under nitrogen. Removal of the excess of butylamine at reduced pressure left a orange oil which was purified by FC (n-hexane/EtOAc 1:1) yielding 0.23 g (64%) of 2-ethylhexyl (1-N-butyl-2,6-dimethyl-1H-pyridin-4-ylidene)cyanoacetate as a slightly yellow solid.

$^1$H-NMR (300 MHZ, CDCl$_3$): 8.20 (s, 1H), 6.86 (s, 1H), 4.05 (m, 2H, —OCH$_2$), 3.85 (t, 2H, —NCH$_2$) 2.45 (s, 6H, CH$_3$), 1.65 (m, 3H), 1.50-1.20(m, 10H), 1.01 (t, 3H, CH$_3$), 0.9 (m, 6H, 2CH$_3$). MS (CI): 359 (M+H$^+$). IR (neat): 2960m, 2929m, 2858w, 2177vs, 1665vs, 1619vs, 1546m, 1501s, 1479s, 1380s, 1354s, 1316m, 1252s, 1190m, 1114m, 1056s (br.) cm$^{-1}$. M.p.: 69-70° C., UV: $\lambda_{max}$=374 nm ($\epsilon$=39'654)

EXAMPLE 8

Preparation of 2-ethylhexyl (1-N-[3-(2-ethylhexyloxy)propyl]-2,6-di-methyl-1H-pyridin-4ylidene)cyanoacetate In analogy to Example 11 there was obtained 2-ethylhexyl (1-N-[3-(2-ethylhexyloxy)-propyl]-2,6-dimethyl-1H-pyridin-4-ylidene)cyanoacetate.

$^1$H-NMR (300 MHZ, CDCl$_3$): 8.20 (s, 1H), 6.85 (s, 1H), 4.05 (m, 2H, —NCH$_2$, —OCH$_2$), 3.46 (t,2H, —OCH$_2$), 3.31 (d, 2H, CH$_2$), 2.45 (s, 6H, CH$_3$), 1.90 (m, 2H), 1.65 (m, 1H), 152-1.20 (m, 17H), 0.89 (m, 12H, 4CH$_3$), 0.9 (m, 6H, 2CH$_3$). MS (CI): 473 (M+H$^+$). IR (neat): 2958m, 2926m, 2858m, 2179m, 1671s, 1620vs, 1547lmI, 1503m, 1483s, 1375m, 1349s, 1307m, 1253vs, 1188m, 1103s, 1053vs, cm$^{-1}$. M.p.: 69-70° C., UV: $\lambda_{max}$=366 nm ($\epsilon$=46'163).

EXAMPLE 9

Preparation of 2-{1-[3-(2-{2-[3-(4-dicyanomethylene-2,6-dimethyl-4H-pyridin-1-yl)-propoxy]-ethoxy}-ethoxy)-propyl]-2,6-dimethyl-1H-pyridin-4-ylidene}-malononitrile A solution of 0.52 g (3 mmol) of (2,6-dimethyl-4H-pyran-4-ylidene)malononitril and 0.3 ml (1.5 mmol) of 4,7,10-trioxa-1,13-tridecanediamine in 6 ml of acetontrile was heated to 90° C. for 70 h under nitrogen. Removal of the acetonitrile left a brown residue which was recrystallized from 25 ml methanol and 10 ml ethyl acetate yielding 0.68 g (43%) of 2-{1-[3-(2-{2-[3-(4-dicyanomethylene-2,6-dimethyl-4H-pyridin-1-yl)-propoxy]-ethoxy}-ethoxy)-propyl]-2,6-dimethyl-1H-pyridin-4-ylidene}-malononitrile.

$^1$H-NMR (300 MHZ, CDCl$_3$): 6.62 (s, 4H, H—C(3), H—C(5)), 4.10 (m, 4H, H—C(1')), 3.62 (s, 8H, —OCH$_2$CH$_2$O—), 3.55 (t, 4H, H—C(3')), 2.50 (s, 6H, —CH$_3$), 2.00 (m, 4H, H—C(2')). MS (CI): 529 (M+H$^+$). IR (neat): 3521w(br.), 2868w, 2191s, 2163s, 1648vs, 1553s, 1504m, 1484w, 1380w, 1357s, 1313w, 1223w, 1192m, 1102m (br.), 1070m, 1037m cm$^{-1}$. M.p.: 138-139° C., UV: $\lambda_{max}$=372 nm ($\epsilon$=67'608).

EXAMPLE 10

Preparation of an Oil-in-water Sun Milk

An oil-in-water sun milk can be prepared with the following ingredients

|   | Ingredients | INCI Nomenclature | % w/w |
|---|---|---|---|
| A | Compound of formula I or II | | 0.1-25 |
|   | Lanette O | Cetearyl Alcohol | 2.00 |
|   | Myritol 318 | Caprylic/capric Triglyceride | 6.00 |
|   | Mineral oil | Mineral oil | 2.00 |
|   | Vitamin E acetate | Tocopheryl Acetate | 1.00 |
|   | Prisorine 3515 | Isostearyl Alcohol | 4.00 |
|   | Edeta BD | Disodium EDTA | 0.10 |
|   | Phenonip | Phenoxyethanol & Methylparaben & Ethylparaben & Propylparaben & Butylparaben | 0.60 |
|   | AMPHISOL K | Potassium Cetyl Phosphate | 2.00 |
| B | Water deionized | Aqua | ad 100 |
|   | 1,2-Propylen Glycol | Propylene Glycol | 5.00 |
|   | Carbopol 981 | Carbomer | 0.30 |
| C | KOH 10% solution | Potassium Hydroxyde | 2.10 |

Procedure: Heat part A) and B) to 85° C. while stirring. When homogeneous, add part B) to A) under agitation. Cool to about 45° C. while stirring. Then add part C). Homogenize at 11000 rpm to achieve a small particle size. Cool to ambient temperature while stirring.

EXAMPLE 11

Preparation of an Oil-in-water Sun Milk with Pigments

An oil-in-water sun milk with pigments is prepared with the following ingredients

|   | Ingredients | INCI Nomenclature | % w/w |
|---|---|---|---|
| A | PARSOL SLX | Dimethico Diethylbenzalmalonate | 6.00 |
|   | Compound of formula I or II | | 0.1-25 |
|   | Neo Heliopan AP | 2,2-(1,4-phenylene)bis-(1H-benzimidazol-4,6-disulfonic acid) | 3.00 |
|   | Tinosorb S | 2,4-Bis((4-(ethyl-hexylox)-2-hydroxy)-phenyl)-6-(4-methoxyphenyl)-1,3,5-triazine | 3.00 |
|   | Lanette O | Cetearyl Alcohol | 2.00 |
|   | Myritol 318 | Caprylic/capric Triglyceride | 6.00 |
|   | Mineral oil | Mineral oil | 2.00 |
|   | Vitamin E acetate | Tocopheryl Acetate | 1.00 |
|   | Prisorine 3515 | Isostearyl Alcohol | 4.00 |
|   | Edeta BD | Disodium EDTA | 0.10 |
|   | Phenonip | Phenoxyethanol & Methylparaben & Ethyl-paraben & Propylparaben & Butylparaben | 0.60 |
|   | AMPHISOL K | Potassium Cetyl Phosphate | 2.00 |
| B | Water deionized | Aqua | ad 100 |
|   | 1,2-Propylen Glycol | Propylene Glycol | 5.00 |
|   | Carbopol 981 | Carbomer | 0.30 |
|   | Tinosorb M | Methylene Bis-Benzotriazolyl Tetramethyl-butylphenol | 6.00 |
| C | KOH 10% solution | Potassium Hydroxyde | 2.10 |

Heat part A) and B) to 85° C. while stirring. When homogeneous, add part B) to A) under agitation. Cool to about 45° C. while stirring Then add part C). Homogenize at 11000 rpm to achieve a small particle size. Cool to ambient temperature while stirring.

EXAMPLE 12

Preparation of a Water-resistant Sun Milk

A water-resistant sun milk is prepared with the following ingredients

| | Ingredients | INCI Nomenclature | % w/w |
|---|---|---|---|
| A | PARSOL SLX | Dimethico Diethylbenzalmalonate | 6.00 |
| | PARSOL 1789 | Butyl Methoxydibenzoylmethane | 2.00 |
| | Compound of formula I or II | | 0.1-25% |
| | Parsol 5000 | 4-Methylbenzylidene Camphor | 4.00 |
| | Parsol MCX | Ethylhexylmethoxycinnamate | 6.00 |
| | Uvinul T 150 | Ethylhexyltriazone | 2.00 |
| | Silicone DC 200/350 cs | Dimethicone | 1.00 |
| | Lanette O | Cetearyl Alcohol | 2.00 |
| | Softisan 100 | Hydrogenated Coco-Glycerides | 3.00 |
| | Tegosoft TN | C12-15 Alkyl Benzoate | 6.00 |
| | Cetiol B | Dibutyl Adipate | 7.00 |
| | Vitamin E acetate | Tocopheryl Acetate | 2.00 |
| | Berkemyol (Grape Seed) | Palmitoyl Grape seed Extract | 1.00 |
| | BHT | BHT | 0.05 |
| | Edeta BD | Disodium EDTA | 0.10 |
| | Phenonip | Phenoxyethanol & Methylparaben & Ethylparaben & Propylparaben & Butylparaben | 0.60 |
| | AMPHISOL | Cetyl Phosphate DEA | 2.00 |
| B | Water deionized | Aqua | ad 100 |
| | Propylene Glycol | Propylene Glycol | 5.00 |
| | Carbopol 980 | Carbomer | 0.30 |
| C | KOH (10% sol.) | Potassium Hydroxide | 1.50 |

Heat part A) and B) to 85° C. while stirring. When homogeneous, add part B) to A) under agitation. Cool to about 45° C. while stirring Then add part C). Homogenize at 11000 rpm to achieve a small particle size. Cool to ambient temperature while stirring.

EXAMPLE 13

Preparation of a Sun Milk for Babies and Children

A sun milk for babies and children is prepared with the following ingredients

| | Ingredients | INCI Nomenclature | % w/w |
|---|---|---|---|
| A | Compound of formula I or II | | 0.1-25 |
| | Titanium Dioxide | Titanium Dioxide microfine | 4.00 |
| | Tegosoft TN | C12-15 Alkyl Benzoate | 5.00 |
| | Silicone 2503 Cosmetic Wax | Stearyl Dimethicone | 2.00 |
| | Cetyl Alcohol | Cetyl Alcohol | 1.00 |
| | Butylated Hydroxytoluene | BHT | 0.05 |
| | Estol GMM 3650 | Glyceryl Myristate | 4.00 |
| | Edeta BD | Disodium EDTA | 0.10 |
| | Phenonip | Phenoxyethanol & Methylparaben & Ethylparaben & Propylparaben & Butylparaben | 0.60 |
| | AMPHISOL A | Cetyl Phosphate | 2.00 |

| | Ingredients | INCI Nomenclature | % w/w |
|---|---|---|---|
| B | Water deionized | Aqua | ad 100 |
| | Carbopol 980 | Carbomer | 10.00 |
| | Glycerine | Glycerine | 3.00 |
| C | KOH sol. 10% | Potassium Hydroxide | 0.50 |

Heat part A) and B) to 85° C. while stirring. When homogeneous, add part B) to A) under agitation. Cool to about 45° C. while stirring Then add part C). Homogenize at 11000 rpm to achieve a small particle size. Cool to ambient temperature while stirring.

EXAMPLE 14

Preparation of a High Protective Sun Milk

A high protective sun milk is prepared with the following ingredients

| | Ingredients | INCI Nomenclature | % w/w |
|---|---|---|---|
| A | PARSOL SLX | Dimethico Diethylbenzalmalonate | 6.00 |
| | PARSOL 1789 | Butyl Methoxydibenzoylmethane | 2.00 |
| | Compound of formula I or II | | 0.1-25% |
| | Parsol 5000 | 4-Methylbenzylidene Camphor | 4.00 |
| | Parsol MCX | Ethylhexylmethoxicinnamate | 6.00 |
| | Uvinul T 150 | Ethylhexyl Triazone | 2.00 |
| | Silicone DC 200/350 cs | Dimethicone | 1.00 |
| | Lanette O | Cetearyl Alcohol | 2.00 |
| | Softisan 100 | Hydrogenated Coco-Glycerides | 3.00 |
| | Tegosoft TN | C12-15 Alkyl Benzoate | 6.00 |
| | Cetiol B | Dibutyl Adipate | 7.00 |
| | Vitamin E acetate | Tocopheryl Acetate | 2.00 |
| | Berkemyol (Grape Seed) | Palmitoyl Grape seed Extract | 1.00 |
| | BHT | BHT | 0.05 |
| | Edeta BD | Disodium EDTA | 0.10 |
| | Phenonip | Phenoxyethanol & Methylparaben & Ethylparaben & Propylparaben & Butylparaben | 0.60 |
| | AMPHISOL K | Potassium Cetyl Phosphate | 2.00 |
| B | Water deionized | Aqua | ad 100 |
| | Propylene Glycol | Propylene Glycol | 5.00 |
| | Carbopol 980 | Carbomer | 0.30 |
| C | KOH (10% sol.) | Potassium Hydroxide | 1.50 |

Heat part A) and B) to 85° C. while stirring. When homogeneous, add part B) to A) under agitation. Cool to about 45° C. while stirring Then add part C). Homogenize at 11000 rpm to achieve a small particle size. Cool to ambient temperature while stirring.

EXAMPLE 15

Preparation of a Water-free Sun Gel

A water-free sun gel is prepared with the following ingredients

| | Ingredients | INCI Nomenclature | % w/w |
|---|---|---|---|
| A | PARSOL MCX | Ethylhexyl Methoxycinnamate | 6.00 |
| | PARSOL 1789 | Butyl Methoxydibenzoylmethane | 4.00 |
| | PARSOL 5000 | 4-Methylbenzylidene Camphor | 4.00 |
| | Compound of formula I or II | | 0.1-25% |
| | Uvasorb HEB | Diethylhexyl Butamido Triazone | 1.50 |
| | Vitamin E acetate | Tocopheryl Acetate | 1.50 |

-continued

| Ingredients | INCI Nomenclature | % w/w |
|---|---|---|
| Tegosoft TN | C12-15 Alkyl Benzoate | 9.00 |
| Elefac I-205 | Ethylhexyldodecyl Neopentanoate | 2.00 |
| Alcohol | Alcohol | ad 100.00 |
| Isopropyl Alcohol | Isopropyl Alcohol | 20.00 |
| B  Klucel MF | Hydroxypropylcellulose | 2.00 |

Heat part A) to 85° C. while stirring. When homogeneous, add part B) to A) under agitation. Cool to ambient temperature while stirring.

EXAMPLE 16

Preparation of a Sun Gel

A sun gel is prepared with the following ingredients

| Ingredients | INCI Nomenclature | % w/w |
|---|---|---|
| A  Pemulen TR-2 | Acrylates/C10-30 Alky Acrylate Crosspolymer | 0.60 |
| Phenonip | Phenoxyethanol & Methylparaben & Ethylparaben & Propylparaben & Butylparaben | 0.60 |
| Edeta BD | Disodium EDTA | 0.1 |
| Aqua | Aqua | ad 100 |
| Compound of formula I or II | | 0.01-25 |
| B  PARSOL MCX | Ethylhexyl Methoxycinnamate | 5.00 |
| PARSOL 1789 | Butyl Methoxydibenzoylmethane | 4.00 |
| PARSOL 340 | Octocrylene | 3.00 |
| Tegosoft TN | C12-15 Alkyl Benzoate | 15.00 |
| Antaron V-216 | PVP/Hexadecene Copolymer | 1.00 |
| Vitamin E acetate | Tocopheryl Acetate | 0.50 |
| Uvinul TiO2 | Titanium Dioxide and Trimethoxycaprylylsilane | 5.00 |
| Butylated Hydroxytoluene | BHT | 0.05 |
| Cremophor RH 410 | PEG-40 Hydrogenated Castor Oil | 0.50 |
| C  Tris Amino | Tromethamine | 0.50 |
| D  Parfum | Parfum | q.s. |

Heat part A) and B) to 85° C. while stirring. When homogeneous, add part B) to A) under agitation. Cool to about 45° C. while stirring. Homogenize at 11000 rpm to achieve a small particle size. Cool to ambient temperature while stirring. Then add part C) and D).

EXAMPLE 17

Preparation of a High Protection Water-in-oil Sun Milk

A high protection water-in-oil sun milk is prepared with the following ingredients

| Ingredients | INCI Nomenclature | % w/w |
|---|---|---|
| A  PARSOL MCX | Ethylhexyl Methoxycinnamate | 6.00 |
| PARSOL 1789 | Butyl Methoxydibenzoylmethane | 2.00 |
| PARSOL 5000 | 4-Methylbenzylidene Camphor | 4.00 |
| Uvinul T 150 | Ethylhexyl Triazone | 2.00 |
| Uvinul TiO2 | Titanium Dioxide and Trimethoxycaprylylsilane | 5.00 |
| Compound of formula I or II | | 0.1-25 |
| Arlacel P 135 | PEG-30 Dipolyhydroxystearate | 2.00 |
| Tegosoft TN | C12-15 Alkyl Benzoate | 5.00 |
| Cosmacol EMI | Di-C12-13 Alkyl Malate | 6.00 |
| Miglyol 840 | Propylene Glycol Dicaprylate/Dicaprate | 6.00 |

-continued

| Ingredients | INCI Nomenclature | % w/w |
|---|---|---|
| Butylated Hydroxytoluene | BHT | 0.05 |
| Phenonip | Phenoxyethanol & Methylparaben & Ethylparaben & Propylparaben & Butylparaben | 0.60 |
| B  Deionized water | Aqua | ad 100 |
| Glycerin | Glycerin | 5.00 |
| Edeta | Disodium EDTA | 0.1 |
| NaCl | Sodium Chloride | 0.30 |
| C  Parsol HS | Phenylbenzyimidazole Sulphonic Acid | 4.00 |
| Water | Aqua | 20.00 |
| Triethanolamine 99%. | Triethanolamine | 2.50 |

Heat part A) and B) to 85° C. while stirring. When homogeneous, add part B) to A) under agitation. Cool to about 45° C. while stirring Then add part C). Homogenize at 11000 rpm to achieve a small particle size. Cool to ambient temperature while stirring.

EXAMPLE 18

Preparation of a Water-in-oil Milk with Pigments

A water-in-oil milk with pigments can be prepared with the following ingredients

| Ingredients | INCI Nomenclature | % w/w |
|---|---|---|
| A  Cremophor WO 7 | PEG-7 Hydrogenated Castor Oil | 6.00 |
| Elfacos ST 9 | PEG-45/Dodecyl Glycol Copolymer | 2.00 |
| Parsol MCX | Ethylhexyl Methoxycinnamate | 5.00 |
| Parsol 1789 | Butyl Methoxydibenzoylmethane | 3.00 |
| Compound of formula I or II | | 0.1-25 |
| Tinosorb S | 2,4-Bis((4-(ethyl-hexylox)-2-hydroxy-phenyl)-6-(4-methoxyphenyl)-1,3,5-triazine | 3.00 |
| Parsol 5000 | 4-Methylbenzylidene Camphor | 4.00 |
| Uvinul TiO2 | Titanium Dioxide and Trimethoxycaprylylsilane | 2.00 |
| Microcrystalline wax | Microcrystalline Wax | 2.00 |
| Miglyol 812 | Caprylic/capric Triglyceride | 5.00 |
| Vitamin E acetate | Tocopheryl Acetate | 1.00 |
| Jojoba oil | Simmondsia Chinensis Seed Oil | 5.00 |
| Edeta BD | Disodium EDTA | 0.10 |
| Butylated Hydroxytoluene | BHT | 0.05 |
| Phenonip | Phenoxyethanol & Methylparaben & Ethylparaben & Propylparaben & Butylparaben | 0.60 |
| B  Water deionized | Aqua | ad 100 |
| Glycerin | Glycerin | 5.00 |
| C  Neo Heliopan AP | | 2.00 |
| Water deionized | Aqua | 20.00 |
| KOH 10% solution | Potassium Hydroxide | 4.00 |

Procedure: Heat part A) and B) to 85° C. while stirring. When homogeneous, add part B) to A) under agitation. Cool to about 45° C. while stirring. Then add part C). Homogenize at 11000 rpm to achieve a small particle size. Cool to ambient temperature while stirring.

EXAMPLE 19

Preparation of a Hair Conditioner

A hair conditioner can be prepared with the following ingredients

|   | Ingredients | INCI Nomenclature | % w/w |
|---|---|---|---|
| A | Lanette O | Cetearyl Alcohol | 3.00 |
|   | Cetiol LC | Coco Caprylate/Caprate | 2.50 |
|   | Phenonip | Phenoxyethanol & Methylparaben & Ethylparaben & Propylparaben & Butylparaben | 0.60 |
|   | Cremophor A6 | Ceteareth-6 & Stearyl Alcohol | 2.00 |
|   | Cremophor A25 | Ceteareth-25 | 2.00 |
|   | Compound of formula I or II |  | 0.1-25 |
| B | Parsol SLX | Dimethico-diethylbenzalmalonate | 1.00 |
|   | Tween 80 | Polysorbate 80 | q.s. |
| C | Water | Aqua | ad. 100 |
|   | EDETA BD | Disodium EDTA | 0.20 |
|   | Carbopol 980 | Carbomer | 0.20 |
| D | Panthenol 75% | Panthenol | 0.50 |
| E | Triethanolamine | Triethanolamine | q.s. 100 |

Procedure: Heat part A) and B) to 85° C. while stirring. When homogeneous, add part B) to A) under agitation. Cool to about 45° C. while stirring. Add part C). Homogenize at 11000 rpm to achieve a small particle size. Cool to ambient temperature while stirring. Then add parts D) and E).

EXAMPLE 20

Preparation of a Protective Day Cream with Vitamin C

A protective Day cream with Vitamin C can be prepared with the following ingredients

|   | Ingredients | INCI Nomenclature | % w/w |
|---|---|---|---|
| A | PARSOL SLX | Dimethico Diethylbenzalmalonate | 4.00 |
|   | PARSOL 1789 | Butyl Methoxydibenzoylmethane | 1.50 |
|   | Glyceryl Myristate | Glyceryl Myristate | 2.00 |
|   | Compound of formula I or II |  | 0.1–25 |
|   | Cetyl Alcohol | Cetyl Alcohol | 0.50 |
|   | Myritol 318 | Caprylic/Capric Triglyceride | 5.00 |
|   | Crodamol DA | Diisopropyl Adipate | 5.00 |
|   | Vitamin E acetate | Tocopheryl Acetate | 2.00 |
|   | Butylated Hydroxytoluene | BHT | 0.05 |
|   | Phenonip | Phenoxyethanol & Methylparaben & Ethylparaben & Propylparaben & Butylparaben | 0.60 |
|   | Edeta BD | Disodium EDTA | 0.10 |
|   | AMPHISOL K | Potassium Cetyl Phosphate | 2.00 |
| B | Water deionized | Aqua | ad 100 |
|   | 1,2-Propylene Glycol | Propylene Glycol | 2.00 |
|   | D-PANTHENOL 75 L | Panthenol | 2.00 |
|   | Ethanol | Ethanol | 5.00 |
|   | Allantoin | Allantoin | 0.20 |
|   | Carbopol ETD 2001 | Carbomer | 0.30 |
| C | KOH 10% sol. | Potassium Hydroxide | 1.50 |
| D | Water | Aqua | 10.00 |
|   | STAY-C 50 | Sodium Ascorbyl Phosphate | 0.50 |
| E | Perfume | Perfume | q.s. |

Procedure: Heat part A) and B) to 85° C. while stirring. When homogeneous, add part B) to A) under agitation. Cool to about 45° C. while stirring. Add part C) . . . Homogenize at 11000 rpm to achieve a small particle size. Cool to ambient temperature while stirring. Then add parts D) and E).

EXAMPLE 21

Preparation of a Pearly Shampoo

A pearly shampoo with Parsol SLX and Phytantriol and the following ingredients can be prepared as follows

|   | Ingredients | INCI Nomenclature | % w/w |
|---|---|---|---|
| A | Texapon NSO-BZ | Sodium Laureth Sulfate | 50.00 |
|   | Carbopol Aqua SF-1 | Acrylates Copolymer | 7.00 |
|   | Parsol SLX | Polysilicone-15 | 1.00 |
|   | Kathon CG | Methylchloroisothiazolinone and Methyl-isothiazolinone | 0.10 |
|   | D-Panthenol 75 L | Panthenol | 0.50 |
|   | Deionized Water | Aqua | 27.40 |
| B | NaOH 30% | Sodium Hydroxide | 1.10 |
| C | Compound of formula I or II |  | 0.1–25 |
|   | Cetiol HE | PEG-7 Glyceryl Cocoate | 1.00 |
|   | Tego Betaine L | Cocamidopropyl Betaine | 5.00 |
|   | Euperlan PK-3000 OK | Glycol Distearate and Glycerine and Laureth-4 and Cocamidopropyl Betaine | 3.00 |
|   | EDETA BD | Disodium EDTA | 0.20 |
|   | FD&C Blue No.1, 1.0% sol. | CI 42090 | 0.01 |
|   | Natrium Chloride | Sodium Chloride | 0.50 |
| D | Cremophor RH 40 | PEG-40 Hydrogenated Castor Oil | 2.00 |
|   | Phytantriol | Phytantriol | 0.20 |
|   | Perfume | Perfume | 1.00 |

Procedure: Part A: Add all the ingredients and mix under slow agitation. Neutralize Part A with Part B until a pH of 6.5 is reached. Part C: Add all the ingredients to AB and mix under slow agitation. Mix Part D together, and add it to ABC under moderate agitation.

What is claimed is:

1. A UV-A screening composition comprising a compound of the general formula I or II

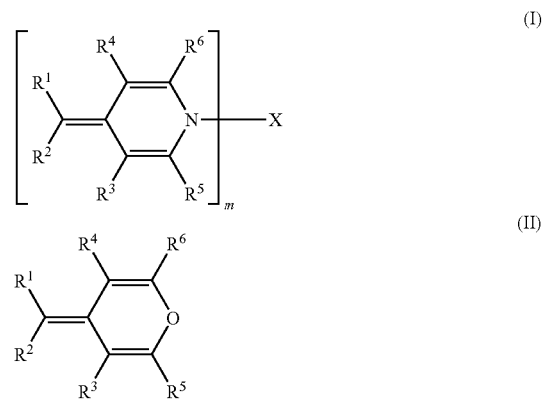

wherein
  m is 1 or 2;
  $R^1$ and $R^2$ are identical or different electron-withdrawing groups, or one of $R^1$ and $R^2$ is hydrogen and the other of $R^1$ and $R^2$ is an electron-withdrawing group;
  $R^3$, $R^4$, $R^5$, and $R^6$ are, independently, hydrogen, alkyl, cycloalkyl or aryl;
  $R^3$ and $R^5$ and/or $R^4$, and $R^6$ taken together with the carbon atoms to which they are attached, form a 5 or 6 membered ring which is unsubstituted or substituted with one to four alkyl, cycloalkyl or alkoxy groups;
  X is a moiety $R^7$, when m is 1, and is alkylene or poly(oxyalkylene) when m is 2; and R⁷ is hydrogen, alkyl, cycloalkyl, alkoxyalkyl or aryl; and a topically applicable, cosmetically acceptable carrier.

2. A composition according to claim 1, wherein the compound of formula I is selected from the group consisting of
1-N-(2-ethylhexyl)-4-dicyanomethylene-2,6-dimethyl-1, 4-dihydropyridine,
1-N-dodecyl-4-dicyanomethylene-2,6-dimethyl-1,4-dihydropyridine,
1-N-[3-(2-ethylhexyloxy)propyl]-4-dicyanomethylene-2, 6-dimethyl-1,4-dihydroyridine,
1-N-[3,5,5-trimethylhexyl]-4-dicyanomethylene-2,6-dimethyl-1,4-dihydropyridine,
1-N-methyl-4-dicyanomethylene-2,6-dimethyl-1,4-dihydropyridine,
1-N-butyl-4-dicyanomethylene-2,6-dimethyl-1,4-dihydropyridine,
2-ethylhexyl (1-Butyl-2,6-dimethyl-1H-pyridin-4-ylidene)cyanoacetate,
2-{1-[3-(2-{2-[3-(4-dicyanomethylene-2,6-dimethyl-4H-pyridin-1-yl)-propoxy]-ethoxy}-ethoxy)-propyl]-2,6-dimethyl-1H-pyridin-4-ylidene}-malononitrile, and
2-ethylhexyl (1-N-[3-(2-Ethylhexyloxy)propyl]-2,6-dimethyl-1H-pyridin-4-ylidene)cyanoacetate.

3. A composition according to claim 1, wherein the compound of formula II is selected from the group consisting of
ethyl (2-6-dimethyl-pyran-4-ylidene) cyanoactate,
2-ethylhexyl (2,6-dimethyl-pyran-4-ylidene)cyanoacetate,
2-(2,6-diethyl-3,5-dimethylpyran-4-ylidene)malononitrile and
2-(3,5-diethyl-2,6-dipropylpyran-4-ylidene)malononitrile.

4. A composition according to claim 1 comprising from 0.5% by weight to 12% by weight of a compound of formula I or II.

5. A composition according to claim 1 further comprising an additional UV-A screening agent and/or UV-B screening agent.

6. A composition according to claim 1 wherein the compound of formula I or II is incorporated into a plastic substrate.

7. A compound of the general formula I according to claim 1 wherein m is 2.

8. A compound of the general formula I or II according to claim 1 selected from the group consisting of
2-{1-[3-(2-{2-[3-(4-dicyanomethylene-2,6-dimethyl-4H-pyridin-1-yl)-propoxy]-ethoxy}-ethoxy)-propyl]-2,6-dimethyl-1H-pyridin-4-ylidene}-malononitrile;
1-N-(2-ethylhexyl)-4-(dicyanomethylene-2,6-dimethyl-1, 4-dihydropyridine;
1-N-dodecyl-4-dicyanomethylene-2,6-dimethyl-1,4-dihydropyridine;
1-N-[3-(2-ethylhexyloxy)propyl]-4-dicyanomethylene-2, 6-dimethyl-1,4-dihydroyridine;
1-N-[3,5,5-trimethylhexyl]-4-dicyanomethylene-2,6-dimethyl-1,4-dihydropyridine;
2-ethylhexyl (2,6-dimethyl-pyran-4-ylidene)cyanoacetate;
2-ethylhexyl (1-N-[3-(2-Ethylhexyloxy)propyl]-2,6-dimethyl-1H-pyridin-4-ylidene)cyanoacetate;

2-(2,6-diethyl-3,5-dimethylpyran-4-ylidene)malononitrile; and
2-(3,5-diethyl-2,6-dipropylpyran-4-ylidene)malononitrile.

9. A composition according to claim 2 comprising from 0.5% by weight to 12% by weight of a compound of formula I.

10. A composition according to claim 3 comprising from 0.5% by weight to 12% by weight of a compound of formula II.

11. A composition according to claim 2 further comprising an additional UV-A screening agent or UV-B screening agent.

12. A composition according to claim 3 further comprising an additional UV-A screening agent or UV-B screening agent.

13. A composition according to claim 2 further comprising a topically applicable, cosmetically acceptable carrier.

14. A composition according to claim 3 further comprising a topically applicable, cosmetically acceptable carrier.

15. A composition according to claim 2 wherein the compound of formula I or II is incorporated into a plastic substrate.

16. A composition according to claim 3 wherein the compound of formula I or II is incorporated into a plastic substrate.

17. A method of protecting a hair or skin comprising applying to a hair or skin a UV-A screening agent comprising a compound of the general formula I or II:

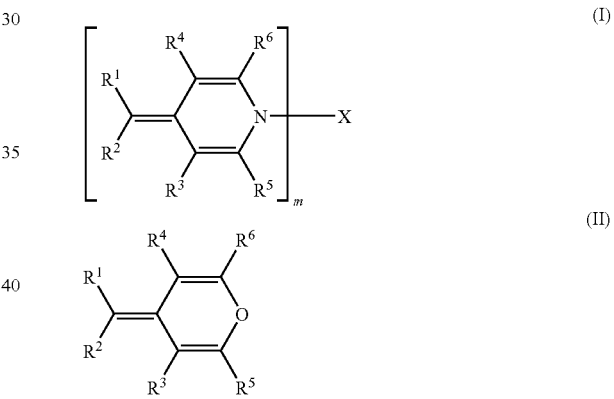

wherein
m is 1 or 2;
R¹ and R² are identical or different electron-withdrawing groups, or one of R¹ and R² is hydrogen and the other of R¹ and R² is an electron-withdrawing group;
R³, R⁴, R⁵, and R⁶ are, independently, hydrogen, alkyl, cycloalkyl or aryl;
R³ and R⁵ and/or R⁴, and R⁶ taken together with the carbon atoms to which they are attached, form a 5 or 6 membered ring which is unsubstituted or substituted with one to four alkyl, cycloalkyl or alkoxy groups;
X is a moiety R⁷, when m is 1, and is alkylene or poly (oxyalkylene) when m is 2; and
R⁷ is hydrogen, alkyl, cycloalkyl, alkoxyalkyl or aryl.

* * * * *